United States Patent [19]
Putz

[11] Patent Number: 4,850,359
[45] Date of Patent: Jul. 25, 1989

[54] ELECTRICAL BRAIN-CONTACT DEVICES

[75] Inventor: David A. Putz, Racine, Wis.

[73] Assignee: Ad-Tech Medical Instrument Corporation, Racine, Wis.

[21] Appl. No.: 128,797

[22] Filed: Dec. 4, 1987

Related U.S. Application Data

[63] Continuation-in-part of Ser. No. 109,111, Oct. 16, 1987, abandoned.

[51] Int. Cl.⁴ .......................... A61B 5/04; A61N 1/05
[52] U.S. Cl. .................................. 128/642; 128/784; 439/791
[58] Field of Search .................. 128/642, 784–786, 128/798, 419 P; 439/790, 791, 794, 796

[56] References Cited
U.S. PATENT DOCUMENTS

| | | | |
|---|---|---|---|
| 3,866,615 | 2/1975 | Hewson | 128/784 |
| 4,245,645 | 1/1981 | Arseneault et al. | 128/642 |
| 4,341,226 | 7/1982 | Peters | 128/784 |
| 4,379,462 | 4/1983 | Borkan et al. | 128/786 |
| 4,461,304 | 7/1984 | Kuperstein | 128/642 |
| 4,516,820 | 5/1985 | Kuzma | 128/784 X |
| 4,712,557 | 12/1987 | Harris | 128/419 P |
| 4,744,371 | 5/1988 | Harris | 128/786 |

Primary Examiner—Lee S. Cohen
Attorney, Agent, or Firm—Peter N. Jansson

[57] ABSTRACT

A brain-contact device (10,12,13) having a multi-electrode tissue-engagement member (14,16), lead wires (32) extending to a terminal mount (36) with an array of lead-wire terminals (38) on it, and a connector (46,46a) including a base (48,48a) with a matching array of take-up terminals (70,70a), a movable yoke (50,50a) forming with the base a terminal-mount space (62,62a), and a device (52,52a) to hold the yoke and base together with the arrays in contact.

29 Claims, 5 Drawing Sheets

ELECTRICAL BRAIN-CONTACT DEVICES

RELATED APPLICATION

This is a continuation-in-part of United States patent application Ser. No. 109,111, filed on Oct. 16, 1987, and entitled IMPROVED ELECTRICAL BRAIN-CONTACT DEVICES now abandoned.

FIELD OF THE INVENTION

This invention is related generally to electrical brain-contact devices such as those used for monitoring intracranial electrical activity to define epileptogenic foci and, more particularly, to means on such devices for facilitating surgical procedures for their placement and set-up, including their electrical connection away from the brain.

BACKGROUND OF THE INVENTION

Surgical removal of epileptogenic brain is indicated for treatment of many medically refractory focal seizure disorders. One important factor in providing good results from such surgery is the degree of accuracy in identifying epileptogenic foci. Various methods and devices have been used in attempting to determine epileptogenic foci. All, of course, involve sensing of intracranial electrical activity using electrical contacts applied in various ways.

Standard scalp contacts have been used for many years, but accurate localization is usually very difficult with recordings obtained from such contacts. In recent years, therefore, many epilepsy centers have adopted techniques using intracranial contacts to better define regions of cortical epileptogenicity.

Intracranial sensing techniques have used, broadly speaking, two different kinds of members for engagement with brain tissue. Such tissue-engagement members include depth probes and flexible flat surface members.

Depth probes, which are often referred to as "depth electrodes," penetrate deep into the brain tissue in direct contact with such tissue. On the other hand, flat flexible surface members, including what are sometimes referred to as "strip" electrodes and "grid" electrodes, are placed subdurally in direct contact with brain tissue at the surface of the brain.

Each of these different kinds of intracranial tissue-engagement members has a plurality of electrodes which are separated from one another by a non-conductive material on which the electrodes are mounted. Separate lead wires extend from the tissue-engagement member for each electrode. Such lead wires extend away from the tissue-engagement member to means for connecting the lead wires with individual conductors, which lead to monitoring or recording equipment.

Depth probes typically have electrode rings sleeved over and spaced along a non-conductive tubular member, with thin insulated wires extending inside the tube to a position away from its tissue-engaging portion. An example of such depth probes is shown in U.S. Pat. No. 4,425,645 (Arseneault et al.).

Strips and grids have a one-dimensional line and a two-dimensional field, respectively, of electrode disks which are arranged and held on a non-conductive flat flexible sheet-like member, usually between two thin sheet-like layers of non-conductive material. Thin insulated wires typically extend between the layers to a proximal edge of the sheet-like member and from there as lead wires away from such tissue-engaging member. An example of such a strip electrode is disclosed in U.S. patent application No. 71,075, now U.S. Pat. No. 4,805,625 (Wyler et al.).

For each type of tissue-engagement member used in the prior art for monitoring electrical activity in the brain, the procedures for placement and hookup are of great importance.

In the case of depth probes, it is essential that the depth probes be inserted with a high degree of accuracy in order to avoid damage to veins and arteries or unnecessary damage to brain tissue which might be caused by insertion and reinsertion. Precision in insertion is also necessary in order that placement be in the most advantageous positions for locating abnormal cells.

In the case of strip and grid electrodes, it is important that the flat flexible member be in proper contact with brain tissue to obtain reliable readings. It is also important that the often rather large opening in the skull, which is necessary for proper placement or insertion of a grid or strip, be well protected from the possibility of infection o that intracranial infection does not occur.

For both depth electrodes and strip or grid electrodes, it is essential that the lead wires extending from the brain-engagement member be properly connected and that the fragile lead wires themselves remain functional, without any breakage or disconnection.

While there has been much progress in the field of electrical brain-contact devices in recent years, existing devices and procedures have a number of problems and drawbacks. For one thing, the surgical placement and set-up procedures which precede the test period are far too time-consuming and complex. Such procedures in some cases also lead to specific problems.

Such problems can be described best by generally describing at least certain parts of the placement and set-up procedures.

One of the early steps in existing placement and set-up procedures for grid and strip electrodes is making an incision in the scalp over the site of proposed electrode placement. Then a burr hole is drilled in the skull or a skull area otherwise removed. One or more incisions are then made in the dura to accommodate placement of a grid or insertion of a strip. Dural tack-up sutures are placed in both dural margins.

The grid or strip electrode is then placed or inserted, with the electrodes in contact with the brain tissue. When strip electrodes are used, a plurality of strips are inserted in each burr hole. After the grid or strips have been positioned, the dural edges are approximated with a suture.

The lead wires, which extend from the proximal end of each strip or grid, are passed through the sutured dura incision. All the wires, one for each electrode on the grid or on every strip, are then brought out through the skin by passing them through a needle and then drawing them through the scalp at a distance (usually 4-5 cm) from the skull opening. When there are numerous wires it is often necessary to tunnel in a number of directions through the scalp to sites spaced from the skull opening. This can be both very time-consuming and very hard on the patient's head. Furthermore, when such wires have exited the scalp at the chosen sites, it then remains necessary to make electrical hookups of each of such wires in the appropriate manner. This is itself a time-consuming operation, and one in which there is a risk of incorrect hookups.

The fragile lead wires are quite susceptible to breakage during these manipulative operations. When this occurs, it may be necessary to reopen the dura to remove and replace the grid or strip from which the lead wire broke, and repeat many of the procedures described above.

In order to minimize the likelihood of lead wire breakage, lead wires of greater size may be used. However, increasing the diameter of the lead wires tends to increase the overall thickness of the strip or grid. Thickness can be undesirable in such flat flexible members and can in some cases pose problems for the electrical sensing operations. Furthermore, increasing wire thickness can substantially increase the cost of the device, particularly if silver or platinum wire is used.

Because of all the problems and difficulties of such wire exit and connection operations, lead wires are sometimes simply brought out of the head right at the point of the skull opening. This procedure results in a greater risk of fluid leakage problems and of dangerous infection occurring at the site of the major wound, near, of course, to the brain by virtue of such opening.

Referring now to the insertion and connection of depth probes, such electrodes have been installed in different ways depending upon the circumstances. In some cases, depth probes are stiffened by means of a stylette which is inserted into the tubular depth probe. The probe is then pushed into the brain tissue, guided by the stylette, and the stylette is then withdrawn. In other cases, such as when a cannula is already in place in the brain tissue, the cannula must be removed in order to accommodate insertion of the depth probe at that site, either with or without the aid of a stylette.

In either case, various securing steps are then carried out. After that, electrical connections are made, either with or without the aid of specialized connector means. Such connection procedures are typically difficult and time-consuming.

There remains a substantial need for an improved electrical brain-contact device overcoming the above problems and difficulties arising during placement and setup procedures.

OBJECTS OF THE INVENTION

It is an object of this invention to provide an improved electrical brain-contact device which overcomes certain problems of prior art devices, including those mentioned above.

Another object of this invention is to provide an improved electrical brain-contact device which facilitates surgical procedures used in locating epileptogenic foci.

Another object of this invention is to provide an improved electrical brain-contact device which may be electrically connected easily and quickly during surgical placement and set-up procedures.

Another object of this invention is to provide an improved electrical brain-contact device which reduces or eliminates lead wire breakage and the related problems.

Another object of this invention is to provide an improved electrical brain-contact device which facilitates placement and set-up of tissue-engagement members having large numbers of electrodes and lead wires.

Another object of this invention is to provide an improved electrical brain-contact device which facilitates accurate insertion of depth probes.

Another object of this invention is to provide an improved electrical brain-contact device allowing accurate insertion of a depth probe using an in-place cannula without prior removal of such cannula.

Another object of this invention is to provide an improved electrical brain-contact device facilitating surgical procedures which minimize the infection risks.

Another object of this invention is to provide an improved electrical brain-contact device which eliminates the need for multiple separate threadings of lead wires in different directions along the scalp, thus eliminating the related scalp damage.

Another object of this invention is to provide an improved electrical brain-contact device having lead wires of substantially reduced diameter.

Another object of this invention is to provide an improved electrical brain-contact device of the strip or grid type having substantially reduced thicknesses.

These and other important objects will be apparent from the descriptions of this invention which follow.

SUMMARY OF THE INVENTION

This invention is an improvement in electrical brain-contact devices of the type having tissue-engagement members with a plurality of electrodes, separate lead wires from the tissue-engagement members for each of their electrodes, and means away from the tissue-engagement members to connect the lead wires with individual conductors. These brain-contact devices may be used to sense and record intracranial electrical discharges and/or to stimulate tissue.

In the brain-contact device of this invention, the lead wires extend from the tissue-engagement member to a terminal mount and to an array of lead-wire terminals which are on and form a part of the terminal mount. A connector especially adapted for the terminal mount includes a base member with an array of take-up terminals matching the array of lead-wire terminals on the terminal mount, a yoke member which is movable with respect to the base member, and means to hold the yoke and base members together with the terminal mount between. This secures the arrays in terminal-to-terminal contact. The base and yoke members together form a space for the terminal mount.

The brain-contact device of this invention greatly facilitates placement and set-up procedures, particularly its electrical connection. Such electrical connection is made quick and simple by the connectors of this invention.

The terminal mount has a non-conductive mount base which is preferably a sheathing with the lead wires (each of which is insulated) in it and the lead-wire terminals spaced along it. The sheathing is most preferably tubular, with the lead-wire terminal rings which are sleeved around the tube and held firmly on the tube. The tubular sheathing preferably extends from the tissue-engagement member for substantially the entire length of the lead wires.

In certain preferred embodiments, the base member of the connector preferably forms terminal niches along the terminal-mount space, with the take-up terminals being within such niches, most preferably extending, when the terminal mount is removed, from the niches into the terminal-mount space. In certain embodiments, the take-up terminals are preferably spring members, such as small coil springs, which are depressed by the terminal mount when the terminal mount is in place.

This preferred arrangement holds the lead-wire terminals and the take-up terminals in firm electrical contact.

In certain preferred embodiments, the base and yoke members have major portions which are semi-cylindroids which together form a cylindroid, and the holding means is a clamp ring extending around the cylindroid. In such configuration, the space for the terminal mount is most preferably along the axis of the cylindroid.

The clamp ring may be in various forms. In one preferred form, the clamp ring has a gap in it large enough such that the lead wires may pass through the gap to facilitate the mounting of the clamp ring on the cylindroid. The clamp ring may readily be brought into axial alignment with the cylindroid by virtue of such gap, and then slid over the cylindroid. The dimensioning and resilient characteristics of the ring allow it to hold the semi-cylindroids firmly together.

In particularly preferred embodiments of the type just described, either the base member or the yoke member has brackets at either end, while the other of such members is dimensioned to be received between such brackets. One of the brackets forms an axial opening receiving the terminal mount, which in such embodiments has tubular sheathing with electrode rings on it.

The tubular sheathing preferably has a marking on it which is alignable with an end bracket, preferably the bracket having the axial opening mentioned above, to facilitate alignment of the lead-wire array with the take-up array. The other bracket may form a stop for the tubular sheathing as an alternate or additional way to facilitate alignment of the terminal arrays. Such other bracket may have its own axial opening to receive and hold the terminal mount in proper position along the axis of the cylindroid. This serves to facilitate proper assembly of the terminal mount with the connector means.

In certain other very highly preferred embodiments of this invention, the base and the yoke are in a very different form having additional significant advantages. In such embodiments, the base is a first block having a first surface and the yoke is a second block having a second surface against the first surface, with at least one of the first and second surfaces having a major groove which forms the space for the terminal mount. The take-up terminals are secured to the first block and extend in spaced fashion across the major groove.

In such embodiments, the blocks are preferably held together by one or more screw members, preferably one as later explained, extending between the first and second blocks. Such screw members, which may be completely removably to allow complete removal of the second block from the first if desired, are used to progressively draw the first and second surfaces of such blocks together. The screws are preferably finger-operable.

In preferred embodiments of the types having blocks, the major groove is preferably in the first surface, that is, in the first block. The second surface is preferably substantially flat, with the terminal mount, the major groove, and the take-up terminals dimensioned and arranged such that drawing the first and second surfaces together clamps the arrays firmly together. More specifically, the depth of the major groove is small enough that, when the blocks are drawn tightly together, the terminal mount is tightly sandwiched between the blocks.

In such embodiments of the invention, there is preferably only one screw member which serves as the sole interconnection of the first and second blocks. Such screw member may extend through the second block freely and be in threaded engagement with the first block. In such embodiments, the screw member may be loosened short of disengagement with the first block such that the second block may be pivoted with respect to the first block to substantially uncover the major groove. This facilitates insertion of the terminal mount when the screw member is loosened. Indeed, loosening and retightening to insert the terminal mount, preferably by finger-turning of the screw member, can be quickly carried out, and with one hand if necessary.

In embodiments of the type having a pair of blocks, as described, the first block has a side surface parallel to the major groove and the take-up terminals are preferably straight wires which are embedded within the first block, extend across the major groove, and terminate in connector ends exposed along the side surface. This facilitates organized electrical connection with the device of this invention, whether by individual connectors or by a multi-contact plug.

One of the blocks, preferably the first, may be marked with colors, numbers, letters or other indicia to identify which contact relates to which electrode in use during a test period.

The first block preferably has one open end and one closed end for the major groove. This facilitates proper alignment of the contact arrays.

Referring again to characteristics of the terminal mount, earlier described, the preferred tubular sheathing which forms the terminal mount preferably has a tapered lead end. Such tapered lead end facilitates various insertion steps, including in some cases insertion through a needle, for purposes hereafter explained, as well as insertion through the axial opening in the preferred bracket, or into the groove in the block-type connector, and insertion over the take-up terminals as the sheathing moves into the connector.

In certain preferred embodiments, a pull line is attached to the terminal mount, such as by connection to the inside of the sheathing forming such terminal mount, and extends from the terminal mount in a direction away from the lead wires. This further facilitates threading of the terminal mount and lead wires through a needle and/or through the aforementioned bracket or groove openings, making surgical procedures that much easier.

In certain embodiments of this invention, the tissue-engagement member is a tubular depth probe. In such cases, the tissue-engaging member is a continuation of the same tubular sheathing which extends over the lead wires and forms a part of the terminal mount, such that the tubular sheathing extends along substantially the entire combined lengths of the depth probe, the lead wires, and the terminal mount. With this essentially completely tubular structure, insertion into the brain is facilitated.

When a stylette is used, it may enter the tubular structure at the end of the preferred tubular terminal mount and extend through the terminal mount, along the lead lines, and through the depth probe until it engages the preferably closed end of the depth probe. When a cannula is already in place in the brain and it is desired to insert a depth probe, the depth probe of this invention can be inserted through the cannula while the cannula is in place. Then, the cannula can be withdrawn over the tubular depth probe, lead line portion, and terminal mount without difficulty. There is no need to withdraw the cannula prior to insertion of the depth probe into the brain tissue.

In each case, connection of the several electrical wires is facilitated by the connector devices of this invention.

In certain other preferred embodiments, the tissue-engagement member is a substantially flat flexible non-conductive member, either a strip or a grid electrode as described above in which the electrodes are flat members on and coplanar with the flexible member. In such embodiments, the lead wires extend within the flexible member to the tubular sheathing at a proximal edge.

The lead wires may be threaded through a needle all at one time, by threading the tubular sheathing which is over them from the site of the dura incision to exit the scalp at a point away from the tissue-engagement member and such incision. Such single threading operation significantly simplifies the surgical procedures. It also reduces any risk of lead wire breakage, because the wires are protected by the full-length sheathing.

Indeed, by virtue of the above configuration, the individual lead wires can be reduced in size. Wires as small as about 0.125 mm in diameter may be used, about one-third the diameter of wire previously used. This allows strip and grid tissue-engagement members to have flexible members less than about 0.30 mm thick, which is much thinner than previous strips and grids. Thin flexible members are believed to be helpful in obtaining accurate readings. The size of the lead wires is removed as a major consideration in determining desirable dimensions of strips and grids.

The aforementioned pull line is particularly useful for strip and grid devices since it is helpful in the threading of the terminal mount through a needle, as described above.

As noted above, the electrical brain-contact device of this invention may be used for stimulation purposes as well as sensing and recording purposes. While the sensing of epileptic discharges is a primary concern, it is to be understood that other sensing applications and uses for stimulation are contemplated.

DETAILED DESCRIPTION OF PREFERRED EMBODIMENTS

The drawings illustrate preferred embodiments of the electrical brain-contact device of this invention, including embodiments with different tissue engagement members and embodiments with different connectors in accordance with this invention. Throughout the drawings, like parts are identified by like numbers. In some cases, comparable parts are identified by like numerals followed by the letter "a."

Three embodiments are illustrated, including a depth probe device 10 shown in FIGS. 1–3 and 5–7, a surface contact device 12 shown in FIGS. 4, 3 and 5–7, and another depth probe device 13 shown in FIGS. 8–12, 2 and 3. Devices 10 and 12 have identical connectors 46 in accordance with this invention, while device 13 has a connector 46a in accordance with another embodiment of this invention.

Devices 10, 12 and 13 all include identical terminal mounts 36, shown in FIGS. 1–3, 5 (in fragment) and 8. The details of terminal mounts 36 are shown best in FIGS. 2 and 3.

Devices 10 and 13 have identical tissue-engagement members, that is, depth probes 14, while surface-contact device 12 has a different tissue-engagement member, namely, flat flexible member 16, sometimes referred to as a "grid electrode." Flat flexible member 16 may be part of a device having a connector like connector 46a, although that is not specifically shown. Depth probes 14 and flat flexible member 16 each place a plurality of electrodes directly in contact with brain cells, to sense electrical discharges.

Depth probe 14 includes a non-conductive hollow plastic tube 18 having electrode rings (or "collars") 20 spaced along it and attached to it. Hollow tube 18 has a closed distal end 22. Individual lead wires extend inside hollow tube 18 from each electrode ring 20 in a direction away from distal end 22. Depth probe 14 itself is of a type known in the prior art.

Flat flexible member 16 includes a flexible sheet member 24, which is formed by a pair of flexible sheets, and a number of flat electrode disks 26 on and coplanar with sheet member 24. Electrode disks 26 are held on sheet member 24 by being placed between its two layers. Individual wires 28 are connected with each electrode 26 and extend toward a proximal edge 30 of flat flexible member 16. Flat flexible member 16 is similar to prior grid and strip electrodes, except that it may be substantially thinner than prior grids and strips.

The wires, such as wires 28, which are within the different types of tissue-engagement members illustrated in the drawings exit such tissue-engagement members as lead wires 32. Lead wires 32 extend from either depth probe 14 or flat flexible member 16 through tubular sheathing 34 to a terminal mount 36. More specifically, lead wires 32 extend to an array of lead-wire terminal rings 38 which form a part of terminal mount 36.

In each of the illustrated embodiments, terminal mount 36 includes tubular sheathing 40 which forms a base for mounting of lead-wire terminal rings 38. Lead wires 32 extend through tubular sheathing 40 in the manner shown in FIG. 3, with each lead wire 32 attached to one lead-wire terminal ring 38.

Tubular sheathing 40, tubular sheathing 34, and hollow tube 18 are all formed of the same tube stock. Such tubing is preferably made of a dielectric silicone material known as SILASTIC, which is available from Dow Chemical Company, Midland, Michigan, or a polyurethane material such as TECOFLEX from Thermedics, Inc., Woburn, Massachusetts. A variety of other suitable non-conductive materials may be used for such tubular members.

Sheet member 24, which forms part of flat flexible member 16, is preferably made of SILASTIC sheeting, available from Dow Chemical Company.

The lead wires extending along and from depth probe 14 or sheet member 24 to and along terminal mount 36 are preferably stainless steel, platinum or silver strands 42 which are insulated by a TEFLON (polytetrafluoroethylene) coating layer 44. See FIG. 3. Such wires, although fragile in themselves, are protected by tubular sheathing 34 and 40 around them. Since they are not individually manipulated such wires are not particularly susceptible to breakage.

Because of the protection of such sheathing, the lead wires may be made much smaller than lead wires in devices of the prior art. In such prior devices, wire has typically been no less than about 0.38 mm in diameter. Given the protection of tubular sheathing 34 and tubular sheathing 40, wires 28 can be as small as about 0.125 mm in diameter. This allows the flexible member to have a thickness of less than about 0.30 mm, making flat flexible member 16 thinner than previous strip and grid electrodes.

As illustrated in FIGS. 1 and 4–7, each of the illustrated brain-contact devices has a connector 46 to which a terminal mount 36 is joined. Connector 46 includes a base member 48, a yoke member 50, which is movable with respect to base member 48, a clamp ring 52, and outlet wires 54 which extend toward connection with monitoring apparatus or the like. Outlet wires 54 are quite strong i comparison with any of the lead wires; they may be freely manipulated and connected as desired without much risk of breakage.

All of yoke member 50 and a major portion 56 of base member 48 are semi-cylindroids which together form a single cylindroid when connector 46 is assembled. Base member 48 and yoke member 50 form first and second semi-cylindrical grooves 58 and 60 which extend alone the axis of the cylindroid. First and second semi-cylindrical grooves 58 and 60 together form cylindrical terminal-mount space 62 which is sized to receive terminal mount 36 when terminal 36 and connector 46 are joined.

Base member 48 has first and second brackets 64 and 66 at opposite ends of its semi-cylindroid portion 56. The spacing of first and second brackets 64 and 66 is such that yoke member 50 fits snugly between such brackets when connector 46 is assembled.

A number of terminal niches 68 are formed in base member 48 in positions spaced along first semi-cylindrical groove 58. Niches 68 are cylindrical and are transverse to the axis of connector 46. Located in each niche 68 is a small coil spring 70. Springs 70 are take-up terminals which extend from niches 68 into terminal-mount space 62 when terminal mount 36 is not present.

Each outlet wire 54 is electrically connected to one and only one take-up terminal 70 at a position in or near the terminal niche 68 containing such terminal 70. Outlet wires 54 extend to take-up terminals 70 through an outward groove 84 which is along the wall of base member 48 at a position adjacent to niches 68. Outlet wires 54 extend through an end opening in second bracket 66, and epoxy within outward groove 84 serves to hold outlet wires 54 and take-up terminal springs 70 in place.

Take-up terminal springs 70 are in an array which matches the array of lead-wire terminals on terminal mount 36. When terminal mount 36 is in place in terminal-mount space 62, such arrays are in terminal-to-terminal contact. When yoke member 50 is assembled with base member 48, terminal rings 38 of terminal mount 36 depress take-up terminal springs 70 toward their respective niches 68. This provides firm electrical contact between take-up terminals 70 and lead-wire terminals 38.

During assembly of yoke member 50 with base member 48, clamp ring 52 is brought into a position of axial alignment with the remainder of connector 46 beyond the end thereof and is then slid over base member 48 and yoke member 50. Clamp ring 52 has a gap 72 in it which is big enough for wires to pass as clamp ring 52 is brought into its position of alignment. The dimensions and resiliency characteristics of clamp ring 52 are such that ring 52 will hold yoke member 50 tightly in place against base member 48. This serves to assure that terminal mount 36 remains properly in place.

Insertion of terminal mount 36 into terminal-mount space 62 requires its insertion through an axial opening in first bracket 64. Such insertion is facilitated by means of tapered lead end 76 of terminal mount 36. Such tapering also facilitates the movement of terminal mount 36 over take-up terminal springs 70 and the insertion of the end of terminal mount 36 into an axial opening 78 in second-bracket 66.

Second bracket 66 itself functions as a stop for engagement by tubular sheathing 40 of terminal mount 36 to facilitate alignment of terminal arrays. Second-bracket axial opening 78 serves to hold terminal mount 36 in the proper position, along the axis, thus facilitating proper assembly of terminal mount 36 with connector 46.

Tapered lead end 76 also facilitates insertion of terminal mount 36 through a needle. This is particularly useful in placement and set-up of electrical brain-contact devices having flat flexible members, the lead wires of which are preferably threaded away from the position of the skull opening.

Figure 1:
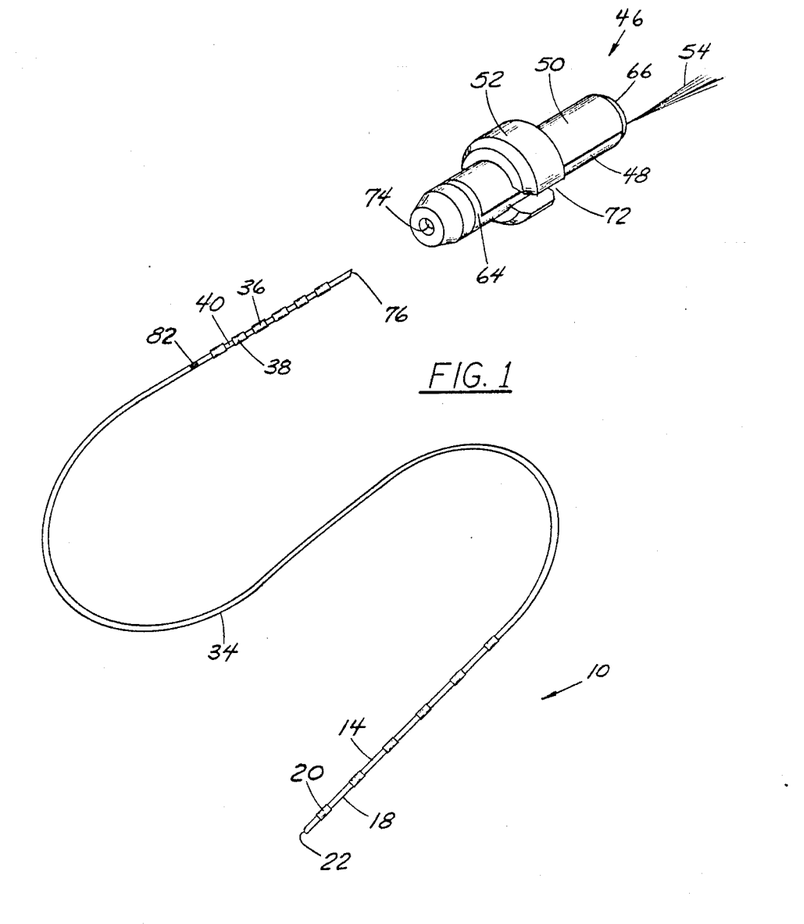
FIG. 1 is perspective view of a electrical depth probe device in accordance with this invention.
Figures 2, 3, 6, 7:
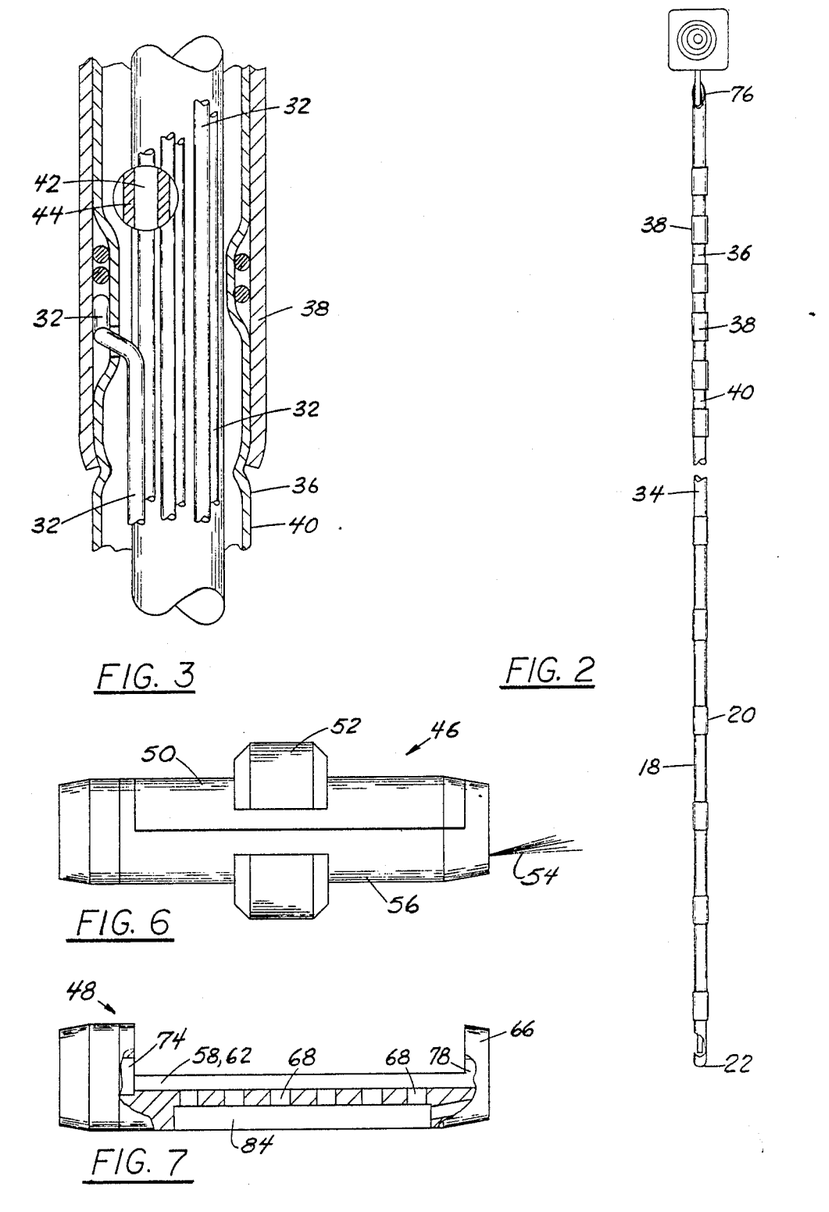
FIG. 2 is an enlarged fragmentary side elevation of the device of FIG. 1 with the connector removed and a stylette inserted.
FIG. 3 is an enlarged fragmentary sectional view of the device shown in FIGS. 1 and 2, a portion thereof which is insertable into the connector.
FIG. 6 is a side elevation of such connector.
FIG. 7 is a side elevation of the base member of such connector, with portions cut away.
Figure 4:
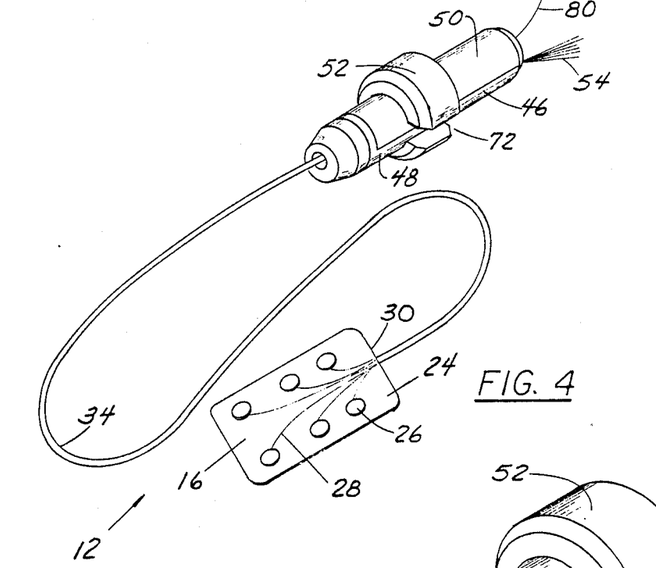
FIG. 4 is perspective view of a grid electrode in device in accordance with this invention.
Figure 5:
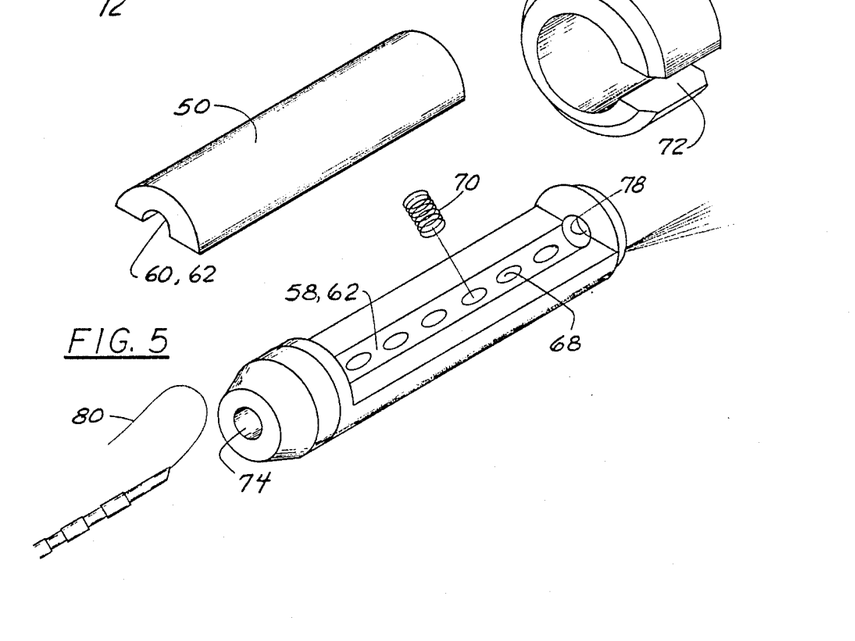
FIG. 5 is an exploded perspective of the connector included in the embodiments of FIGS. 1 and 4, for which the connectors are identical.
Figure 8:
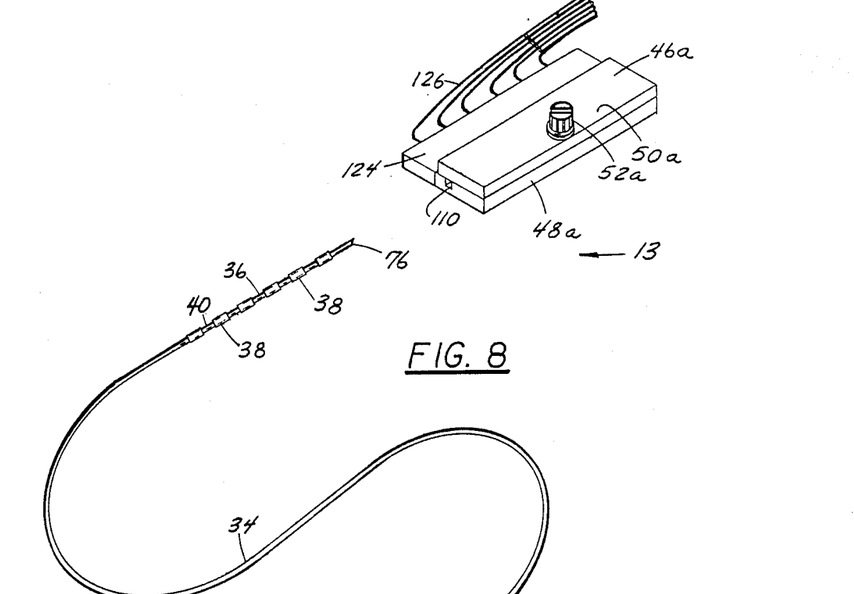
FIG. 8 is a perspective view, similar to FIG. 1, of another embodiment, having another connector in accordance with this invention.
Figure 9:
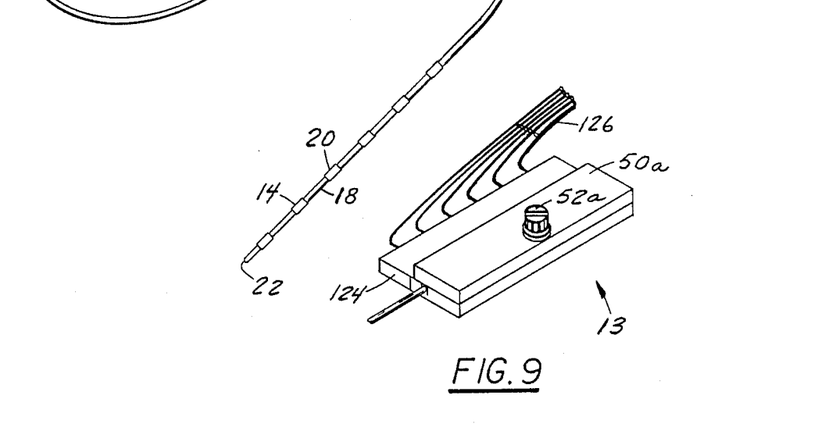
FIG. 9 is a fragmentary view of the device of FIG. 8, but showing the terminal mount inserted into the connector.
Figure 10:
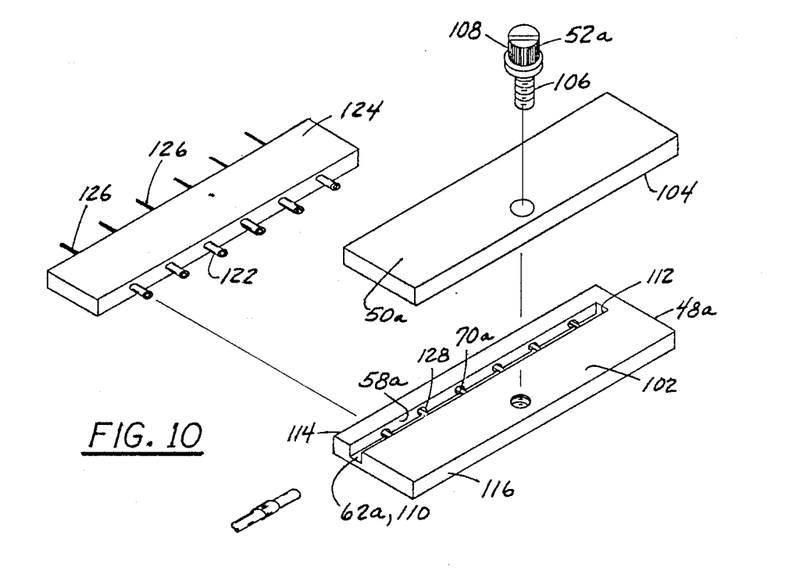
FIG. 10 is an exploded view of the connector of FIG. 8.
Figure 11:
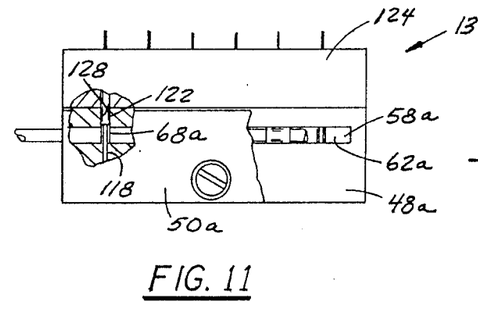
FIG. 11 is a partially cutaway plan view of the connector of FIG. 8.
Figure 12:
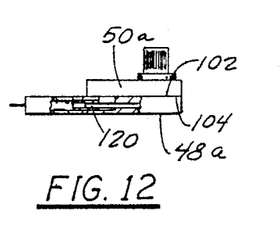
FIG. 12 is a partially cutaway end view of the connector of FIG. 8.

As illustrated in FIGS. 4 and 5, a pull line 80 is attached to terminal mount 36 inside tubular sheathing 40 and extends away from terminal mount 36 in a direction away from its lead wires. Such pull line, which is preferably a flexible, insulated multi-stranded metallic wire of somewhat heavier gauge than the lead wires, is another means to facilitate the threading of terminal mount 36 and tubular sheathing through a needle, or for that matter through axial openings 74 and 78. Pull line 80, which is small in dimension compared to terminal mount 36 and tubular sheathing 34, is first threaded through the needle, or axial opening, and then used to pull terminal mount 36 and tubular sheathing 34 therethrough.

While alignment of the terminal arrays may be accomplished visually or by means of a stop member such as second bracket 66, alignment may also be facilitated by the presence of a marking 82 on tubular sheathing 40. Marking 82, which may be a numbered and/or colored band or suitable marking of any other kind, is located in a position such that its alignment with the end of terminal mount 36 or with some marking on terminal mount 36 causes proper alignment of the terminal arrays.

Turning now to a more detailed description of FIGS. 8-12, connector 46a of depth probe device 13 includes a base block 48a (sometimes referred to herein as first block 48a) a yoke block 50a (sometimes referred to herein as second block 50a), which is movable with respect to base block 48a, and a finger screw 52a. Base block 48a and yoke block 50a are flat rectangular blocks which are drawn together and held together by finger screw 52a.

First or base block 48a and second or yoke block 50a have first and second surfaces 102 and 104, respectively, which are facing each other. Second surface 104 is against first surface 102. Yoke block 50a has a hole through it, in a generally central position, which freely receives the shank 106 of finger screw 52a. Base block 48a has a threaded opening which is engaged by shank 106, which is threaded. Adjustment of finger screw 52a tightens and loosens the relationship of blocks 48a and 50a and also allows complete removal of block 50a. Finger screw 52a has a head which allows easy finger adjustment.

First surface 102 of base block 48a has a major groove 58a in it extending from an open end 110 at one end of base block 48a to a closed end 112 near the opposite end of base block 48a. Major groove 58a, itself in the shape of a rectangular block, forms a terminal-mount space 62a which is sized to receive terminal mount 36 when terminal 36 and connector 46a are joined.

Second surface 104, which adjoins major groove 58a, is flat, and forms a boundary for terminal-mount space 62a. Second surface 104 could, however, have a groove adjacent to the groove in first surface 102; in such case the grooves would together form the terminal-mount space. However, having second surface 104 flat is preferred for ease of use. Surfaces 102 and 104 may have small mating male and female features which, when the blocks are drawn together, tend to hold them in proper alignment.

For each lead-wire terminal ring 38 of terminal mount 36, base block 48a has a take-up terminal 70a which is secured to the block and extends across major groove 58a. Take-up terminals 70a are fairly rigid wires spaced along major groove 58a in an arrangement corresponding to the spacing of terminal rings 38 along terminal mount 36. Take-up terminal wires 70a are of diameter significantly less than the depth of major groove 58a.

For each wire 70a there is a shallow transverse groove 68a in the bottom of major groove 58a, with the wire lying in it. The depth of transverse grooves 68a are much less than the diameters of wires 70a, such that wires 70a extend well above the bottom of major groove 58a.

Terminal mount 36, the depth of major groove 58a, and take-up terminal wires 70a are dimensioned and arranged such that bringing first and second surfaces 102 and 104 of blocks 48a and 50a together clamps the array of lead-wire terminals 38 firmly against the corresponding array of take-up terminals 70a.

First or base block 48a has first and second side surfaces 114 and 116 which are parallel to major groove 58a. Take-up terminals 70a are straight wires which have first end portions 118 (see FIG. 11) embedded in base block 48a in the area between major groove 58a and second side surface 116. Take-up terminal wires 70a are exposed, as indicated, along major groove 58a, and extend on to terminate at connector ends 120 which are exposed along first side surface 114.

Connector ends 120 are supported in generally concentric fashion within small cylindrical openings 128 spaced along first side surface 114 in position to receive annular prongs 122 of a hook-up bar 124 from which wires 126 extend to monitoring equipment. Instead of hook-up bar 124, individual wires can be connected to connector ends 120.

When terminal mount 36 is inserted into major groove 58a its end comes into engagement with closed end 112 of groove 58a. When this occurs, lead-wire terminal rings 38 are in proper alignment with take-up terminals 70a. This further facilitates connection.

The improved electrical brain-contact devices of this invention may be made using well-known materials and construction techniques. Acceptable materials and techniques would be apparent to those skilled in the art who are familiar with this invention.

Many variations are possible. For example, the connectors can vary significantly as long as the connector and terminal mount are adapted for each other. Strips may be used instead of the grids and depth probes which are illustrated. Large grids can have more than one grouping of lead wires within a sheathing, with a separate connector for each grouping. A great number of variations may be made in many of the parts and structures of this invention.

While the principles of this invention have been described in connection with specific embodiments, it should be understood clearly that these descriptions are made only by way of example and are not intended to limit the scope of the invention.

What is claimed is:

1. In an electrical brain-contact device of the type having a tissue-engagement member with a plurality of electrodes, separate lead wires from the tissue-engagement member for each electrode, and means away from the tissue-engagement member to connect the lead wires with individual conductors, the improvement comprising:

the lead wires extending from the tissue-engagement member to a terminal mount and to a linear array of lead-wire terminals on and forming a part of the terminal mount; and the connector means including:

a base member with a matching array of take-up terminals;

a yoke member movable with respect to the base member, said base member and yoke member forming therebetween a space for the terminal mount, said take-up terminals extending from the base member into said space; and means to removably draw and hold the yoke and base members together with the arrays in terminal-to-terminal contact, said holding and drawing means acting through the lead-wire terminals to move the take-up terminals in a direction away from said space and establish good electrical contact between said lead-wire terminals and said take-up terminals, whereby electrical connection of brain-contact devices is facilitated.

2. The electrical brain-contact device of claim 1 wherein the terminal mount comprises a sheathing with the lead wires therein and the lead-wire terminals spaced therealong.

3. The electrical brain-contact device of claim 2 wherein the sheathing is tubular and the lead-wire terminals are rings therearound.

4. The electrical brain-contact device of claim 3 wherein the tubular sheathing extends from the tissue-engagement member for substantially the entire length of the lead wires.

5. The electrical brain-contact device of claim 4 wherein the terminal mount has a tapered lead end thereby facilitating various insertion steps such as insertion through a needle and insertion into the terminal-mount space in the connector means over the take-up terminals.

6. The electrical brain-contact device of claim 4 wherein the tissue-engagement member is a tubular depth probe which is a continuation of the sheathing such that the tubular sheathing extends along substantially the entire combined lengths of the depth probe, the lead wires, and the terminal mount, whereby insertion into the brain is facilitated when using a stylette within such tubular sheathing and/or when inserting through a cannula already in place.

7. The electrical brain-contact device of claim 4 wherein:
the tissue-engagement member is a substantially flat flexible non-conductive member having a proximal edge;
the electrodes are flat members on and coplanar with the flexible member; and
the lead wires extend within the flexible member to the tubular sheathing at the proximal edge, whereby the lead wires may be threaded at one time through a needle to exit the scalp at a site removed from the tissue-engagement member.

8. The electrical brain-contact device of claim 7 wherein the flexible member thickness is less than about 0.30 mm.

9. The electrical brain-contact device of claim 2 wherein:
the base and yoke members have major portions which are semi-cylindroids which together form a cylindroid; and
the holding means is a clamp ring extending around the cylindroid.

10. The electrical brain-contact device of claim 9 wherein the clamp ring has a gap of dimension enough such that the lead wires may pass therethrough to facilitate mounting of the clamp ring.

11. The electrical brain-contact device of claim 9 wherein the terminal-mount space is along the axis of the cylindroid.

12. The electrical brain-contact device of claim 11 wherein:
the base member forms terminal niches along the terminal-mount space;
the take-up terminals, when the terminal mount is removed, extend from the niches into the terminal-mount space; and
the take-up terminals are depressed by the terminal mount, when the terminal mount is in place, such that the lead-wire terminals are in firm electrical contact with the take-up terminals.

13. The electrical brain-contact device of claim 12 wherein:
the sheathing is tubular and the lead-wire terminals are rings therearound;

one of the base and yoke members has brackets at either end, the other of such members being receivable between the brackets; and
one of the brackets forms a substantially axial opening receiving the tubular sheathing.

14. The electrical brain-contact device of claim 13 wherein the sheathing has a marking thereon to facilitate alignment of the arrays.

15. The electrical brain-contact device of claim 13 wherein the other bracket forms a stop for the tubular sheathing, whereby alignment of the arrays is facilitated.

16. The electrical brain-contact device of claim 13 wherein the other bracket forms an axial opening to receive and hold the terminal mount along the axis of the cylindroid, thereby facilitating proper assembly of the terminal mount with the connector means.

17. The electrical brain-contact device of claim 2 wherein:
the base member is a first block having a substantially planar first surface;
the yoke member is a second block having a substantially planar second surface against the first surface;
at least one of the first and second surfaces has a major groove extending thereacross to form the space for the terminal mount; and
the take-up terminals are secured to the first block and extend in spaced fashion across the major groove.

18. The electrical brain-contact device of claim 20 wherein the first surface includes the major groove.

19. The electrical brain-contact device of claim 18 wherein the second surface is substantially flat, the terminal mount, the major groove, and the take-up terminals dimensioned and arranged such that drawing the first and second surfaces together clamps the arrays firmly together.

20. The electrical brain-contact device of claim 19 wherein the first block has one open end and one closed end for the major groove, thereby to facilitate proper alignment of the arrays.

21. The electrical brain-contact device of claim 1 wherein:
the base member forms terminal niches along the terminal-mount space;
the take-up terminals, when the terminal mount is removed, extend from the niches into the terminal-mount space; and
the take-up terminals are depressed by the terminal mount, when the terminal mount is in place, such that the lead-wire terminals are in firm electrical contact with the take-up terminals.

22. In an electrical brain-contact device of the type having a tissue-engagement member with a plurality of electrodes, separate lead wires from the tissue-engagement member for each electrode, and means away from the tissue-engagement member to connect the lead wires with individual conductors, the improvement comprising:
the lead wires extending from the tissue-engagement member to a terminal mount and to an array of lead-wire terminals on and forming a part of the terminal mount, said terminal mount being a tubular sheathing extending from the tissue-engagement member for substantially the entire length of the lead wires and having the lead wires therein, and said lead-wire terminals being rings around and spaced along said sheathing;

the conductor means including a base member with a matching array of take-up terminals, a yoke member movable with respect to the base member and forming therebetween a space for the terminal mount, and means to hold the yoke and base members together with the arrays in terminal-to-terminal contact; and a pull line attached to the terminal mount inside the sheathing thereof and extending from the terminal mount in a direction away from the lead wires, whereby electrical connection of brain-contact devices is facilitated.

23. The electrical brain-contact device of claim 22 wherein:

the tissue-engagement member is a substantially flat flexible non-conductive member having a proximal edge;

the electrodes are flat members on and coplanar with the flexible member; and the lead wires extend within the flexible member to the tubular sheathing at the proximal edge, whereby the lead wires may be threaded at one time through a needle to exit the scalp at a site removed from the tissue-engagement member.

24. In an electrical brain-contact device of the type having a tissue-engagement member with a plurality of electrodes, separate lead wires from the tissue-engagement member for each electrode, and means away from the tissue-engagement member to connect the lead wires with individual conductors, the improvement comprising:

the lead wires extending from the tissue-engagement member to a terminal mount and to an array of lead-wire terminals on and forming a part of the terminal mount, said terminal mount being a sheathing with the lead wires therein and said lead-wire terminals spaced therealong; and the connector means including: a first block having first surface and an array of take-up terminals matching the array of lead-wire terminals, a second block having a second surface against the first surface, said second block movable with respect to the first block, at least one of the first and second surfaces having a major groove which forms between the first and second surfaces a space for the terminal mount, said take-up terminals secured to the first block and extending in spaced fashion across the major groove, and a screw member extending between the first and second blocks to progressively draw the first and second surfaces together with the arrays in terminal-to-terminal contact, whereby electrical connection is facilitated.

25. The electrical brain-contact device of claim 24 wherein the first surface includes the major groove, the second surface is substantially flat, and the terminal mount, the major groove and the take-up terminals are dimensioned and arranged such that drawing the first and second surfaces together clamps the arrays firmly together.

26. The electrical brain-contact device of claim 25 wherein there is only one screw member as the sole interconnection of the first and second blocks such that the second block is pivotable with respect to the first block to substantially uncover the major groove to facilitate insertion of the terminal mount when the screw member is loosened.

27. In an electrical device of the type having a tissue-engagement member with a plurality of electrodes, separate lead wires from the tissue-engagement member for each electrode, and means away from the tissue-engagement member to connect the lead wires with individual conductors, the improvement comprising:

the lead wires extending from the tissue-engagement member to a terminal mount and to an array of lead-wire terminals on and forming a part of the terminal mount, said terminal mount being a sheathing with the lead wires therein and said lead-wire terminals spaced therealong; and the connector means including:

a first block having first surface and an array of take-up terminals matching the array of lead-wire terminals, a second block movable with respect to the first block and including a substantially flat second surface, the first surface having a major groove which forms between the first and second surfaces a space for the terminal mount, the first block having a side surface parallel to the major groove, said take-up terminals being substantially straight wires embedded in the first block, extending in spaced fashion across the major groove, and terminating in connector ends exposed along the side surface, and means to hold the first and second blocks together with the arrays in terminal-to-terminal contact, the terminal mount, major groove and take-up terminals dimensioned and arranged such that drawing the first and second surfaces together clamps the arrays firmly together, whereby electrical connection is facilitated.

28. The electrical brain-contact device of claim 27 wherein the holding means comprises a screw member extending between the first and second blocks to progressively draw the first and second surfaces together.

29. The electrical brain-contact device of claim 28 wherein there is only one screw member as the sole interconnection of the first and second blocks such that the second block is pivotable with respect to the first block to substantially uncover the major groove to facilitate insertion of the terminal mount when the screw member is loosened.

* * * * *

UNITED STATES PATENT AND TRADEMARK OFFICE
CERTIFICATE OF CORRECTION

PATENT NO. : 4,850,359

DATED : July 25, 1989

INVENTOR(S) : David A. Putz

It is certified that error appears in the above-identified patent and that said Letters Patent is hereby corrected as shown below:

Column 1, line 8, change "DEVICES" to --DEVICES,--.

Column 2, line 22, change "infection o" to --infection so--.

Column 9, line 42, change "strong i" to --strong in--.

Column 9, line 49, change "alone" to --along--.

Column 10, line 30, change "opening" to --opening 74--.

Column 11, line 8, change "48a)" to --48a),--.

Column 14, line 30, change "20" to --17--.

Column 15, line 1, change "conductor" to --connector--.

Correct the formatting of claims 1, 7, 24 and 27 as follows:
Continued on next page.

UNITED STATES PATENT AND TRADEMARK OFFICE
CERTIFICATE OF CORRECTION

PATENT NO. : 4,850,359

DATED : July 25, 1989

INVENTOR(S) : David A. Putz

It is certified that error appears in the above-identified patent and that said Letters Patent is hereby corrected as shown below:

1. In an electrical brain-contact device of the type having a tissue-engagement member with a plurality of electrodes, separate lead wires from the tissue-engagement member for each electrode, and means away from the tissue-engagement member to connect the lead wires with individual conductors, the improvement comprising:
the lead wires extending from the tissue-engagement member to a terminal mount and to an a linear array of lead-wire terminals on and forming a part of the terminal mount; and the connector means including:
  a base member with a matching array of take-up terminals,;
  a yoke member movable with respect to the base member, and said base member and yoke member forming therebetween a space for the terminal mount, said take-up terminals extending from the base member into said space; and
  means to removably draw and hold the yoke and base members together with the arrays in terminal-to-terminal contact, said holding and drawing means acting through the lead-wire terminals to move the take-up terminals in a direction away from said space and establish good electrical contact between said lead-wire terminals and said take-up terminals,
whereby electrical connection of brain-contact devices is facilitated.

7. The electrical brain-contact device of claim 4 wherein:
  the tissue-engagement member is a substantially flat flexible non-conductive member having a proximal edge;
  the electrodes are flat members on and coplanar with the flexible member; and
  the lead wires extend within the flexible member to the tubular sheathing at the proximal edge,
whereby the lead wires may be threaded at one time through a needle to exit the scalp at a site removed from the tissue-engagement member.

UNITED STATES PATENT AND TRADEMARK OFFICE
CERTIFICATE OF CORRECTION

PATENT NO. : 4,850,359

DATED : July 25, 1989

INVENTOR(S) : David A. Putz

It is certified that error appears in the above-identified patent and that said Letters Patent is hereby corrected as shown below:

24. In an electrical brain-contact device of the type having a tissue-engagement member with a plurality of electrodes, separate lead wires from the tissue-engagement member for each electrode, and means away from the tissue-engagement member to connect the lead wires with individual conductors, the improvement comprising:
    the lead wires extending from the tissue-engagement member to a terminal mount and to an array of lead-wire terminals on and forming a part of the terminal mount, said terminal mount being a sheathing with the lead wires therein and said lead-wire terminals spaced therealong; and
    the connector means including:
        a first block having first surface and an array of take-up terminals matching the array of lead-wire terminals,
        a second block having a second surface against the first surface, said second block movable with respect to the first block, at least one of the first and second surfaces having a major groove which forms between the first and second surfaces a space for the terminal mount, said take-up terminals secured to the first block and extending in spaced fashion across the major groove, and
        a screw member extending between the first and second blocks to progressively draw the first and second surfaces together with the arrays in terminal-to-terminal contact,
whereby electrical connection is facilitated.

UNITED STATES PATENT AND TRADEMARK OFFICE
CERTIFICATE OF CORRECTION

PATENT NO. : 4,850,359

DATED : July 25, 1989

INVENTOR(S) : David A. Putz

It is certified that error appears in the above-identified patent and that said Letters Patent is hereby corrected as shown below:

27. In an electrical device of the type having a tissue-engagement member with a plurality of electrodes, separate lead wires from the tissue-engagement member for each electrode, and means away from the tissue-engagement member to connect the lead wires with individual conductors, the improvement comprising:

the lead wires extending from the tissue-engagement member to a terminal mount and to an array of lead-wire terminals on and forming a part of the terminal mount, said terminal mount being a sheathing with the lead wires therein and said lead-wire terminals spaced therealong; and     the connector means including:

a first block having first surface and an array of take-up terminals matching the array of lead-wire terminals,         a second block movable with respect to the first block and including a substantially flat second surface,         the first surface having a major groove which forms between the first and second surfaces a space for the terminal mount,         the first block having a side surface parallel to the major groove,         said take-up terminals being substantially straight wires embedded in the first block, extending in spaced fashion across the major groove, and terminating in connector ends exposed along the side surface, and means to hold the first and second blocks together with the arrays in terminal-to-terminal contact, the terminal mount, major groove and take-up terminals dimensioned and arranged such that drawing the first and second surfaces together clamps the arrays firmly together,

UNITED STATES PATENT AND TRADEMARK OFFICE
CERTIFICATE OF CORRECTION

PATENT NO. : 4,850,359

DATED : July 25, 1989

INVENTOR(S) : David A. Putz

Page 5 of 5

It is certified that error appears in the above-identified patent and that said Letters Patent is hereby corrected as shown below:

whereby electrical connection is facilitated.

Signed and Sealed this

Twenty-second Day of May, 1990

Attest:

Attesting Officer

HARRY F. MANBECK, JR.

Commissioner of Patents and Trademarks